United States Patent [19]
Inoue et al.

[11] Patent Number: 6,104,431
[45] Date of Patent: Aug. 15, 2000

[54] VISUAL AXIS DETECTING APPARATUS AND METHOD INCLUDING SCANNING LIGHT SOURCE, AND IMAGE DEVICE USING SAME

[75] Inventors: Shunsuke Inoue, Yokohama; Mamoru Miyawaki, Isehara, both of Japan

[73] Assignee: Canon Kabushiki Kaisha, Tokyo, Japan

[21] Appl. No.: 08/881,079

[22] Filed: Jun. 24, 1997

Related U.S. Application Data

[63] Continuation of application No. 08/658,400, Jun. 5, 1996, abandoned, which is a continuation of application No. 08/329,863, Oct. 27, 1994, abandoned.

[30] Foreign Application Priority Data

Oct. 29, 1993 [JP] Japan ................................. 5-272107

[51] Int. Cl.[7] ................................................. H04N 5/225
[52] U.S. Cl. ............................ 348/333; 348/207; 396/51
[58] Field of Search .................................. 348/207, 219, 348/333, 334; 396/51, 373, 378; 351/210; H04N 5/225

[56] References Cited

U.S. PATENT DOCUMENTS

| | | | |
|---|---|---|---|
| 3,450,466 | 6/1969 | Streisinger | 351/7 |
| 3,864,030 | 2/1975 | Cornsweet | 351/7 |
| 4,373,787 | 2/1983 | Crane et al. | 351/210 |
| 5,129,400 | 7/1992 | Makino et al. | 351/210 |
| 5,214,466 | 5/1993 | Nagano et al. | 354/402 |
| 5,335,035 | 8/1994 | Maeda | 354/219 |
| 5,382,989 | 1/1995 | Uomori et al. | 351/210 |
| 5,386,258 | 1/1995 | Nagano | 354/219 |

FOREIGN PATENT DOCUMENTS

| | | |
|---|---|---|
| 0284225 | 9/1988 | European Pat. Off. . |
| 0602895 | 6/1994 | European Pat. Off. . |
| 1-241511 | 9/1989 | Japan . |

*Primary Examiner*—Tuan Ho
*Attorney, Agent, or Firm*—Fitzpatrick, Cella, Harper & Scinto

[57] ABSTRACT

A visual axis detecting method and apparatus comprising a device that illuminates an eye of an observer with a scanning light source, a photoelectric conversion device that receives reflection light from the eye of the observer, and an arithmetic device that detects Purkinje images and an iris image or a pupil image of the observer's eye on the basis of an output from the photoelectric conversion device, and that detects a direction of a visual axis of the observer from positions of the detected images.

53 Claims, 12 Drawing Sheets

UNIT LED ELEMENT

FIRST PURKINJE IMAGE 3.990
SECOND PURKINJE IMAGE 4.017
FOURTH PURKINJE IMAGE 4.251
THIRD PURKINJE IMAGE 10.452

VISUAL AXIS DETECTING APPARATUS AND METHOD INCLUDING SCANNING LIGHT SOURCE, AND IMAGE DEVICE USING SAME

This application is a continuation of application Ser. No. 08/658,400 filed Jun. 5, 1996, which is a continuation of application Ser. No. 08/329,863 filed Oct. 27, 1994, both now abandoned.

BACKGROUND OF THE INVENTION

1. Field of the Invention

The present invention relates to a visual axis detecting method for detecting the observer's visual axis, a visual axis detecting means, and an image device having the visual axis detecting means, for example, a camera such as a still camera or a video camera, a display device such as a goggle type display, etc.

2. Related Background Art

Many proposals have been made on the technology to facilitate interfaces between various devices and a man by detecting the direction of the visual axis of the man. Among them, the detection of visual axis is relatively easy with an apparatus such as image devices constructed in such a manner that a man looks into a display screen.

For example, Japanese Laid-open Patent Application No. 1-241511 discloses the invention concerning a camera provided with a visual axis detecting apparatus, which is recently brought into actual use. FIG. 13 shows a schematic diagram of the visual axis detecting apparatus as described in the above application.

In FIG. 13, reference numeral 1 designates an objective lens, which is represented by a single lens for convenience' sake but which is actually constructed of a number of lenses, as well known. Numeral 2 denotes a main mirror, which is obliquely set in or is withdrawn from a photo-taking optical path, depending upon whether the camera is in an observing state or in a photo-taking state. Numeral 3 denotes a submirror, which reflects a beam of light having passed through the main mirror 2 down toward the camera body not shown. Further, 4a is a shutter, 4b a stop disposed in the objective lens 1, and 4c a driving mechanism for moving the objective lens 1 along the optical axis for focusing.

Numeral 5 represents a photosensitive member, which is a silver-salt film, a solid state image sensing device such as a CCD or MOS image sensor, or a camera tube such as a vidicon.

Further, 6a is a focus detecting unit.

There is an eyepiece lens 9 disposed behind the exit plane of a pentagonal roof prism 8 for changing the finder optical path, which is used to observe a focus plate 7 by the observer's eye 15. Numeral 10 represents an optical splitter, which is, for example, a dichroic mirror for reflecting infrared light and which is disposed in the eyepiece lens 9. Numeral 11 denotes a condenser lens, 12 an optical splitter such as a half mirror, and 13 an illumination light source such as LED, which preferably emits infrared light (and near infrared light). A beam of light emitted from the infrared illumination light source 13 is changed into a beam of parallel rays advancing along the finder optical path by the power of the condenser lens 11 and the rear surface (observer-side surface) of the eyepiece lens 9. Numeral 14 is a photoelectric converter.

Light having passed through the objective lens 1 is reflected by the main mirror 2 to pass through the focus plate 7 and then to repeat reflection inside the pentagonal roof prism 8. After that, the light enters the observer's eyeball 15 looking into the eyepiece lens 9.

Since surfaces in the human eye have such changes of refractive index as shown in FIG. 14, the illumination light is reflected with different intensities depending upon a magnitude of index change. That is, the light is reflected with intensities decreasing in the order of the front surface of the cornea, the front surface and rear surface of the eye lens, and the rear surface of the cornea. It is also seen from results of trace of paraxial rays that with respect to the front of the eyeball, positions of reflected images from the respective surfaces with incidence of parallel rays are as shown in FIG. 15. These images are called Purkinje images, which are numbered in order from the front surface of the cornea as a first Purkinje image, a second Purkinje image, . . . . As apparent from FIG. 15, the three Purkinje images excluding the third image are concentrated immediately after the third surface, i.e., the front surface of the eye lens, and from the study on the index change as described, the reflection images have the respective intensities decreasing in the order of the first image, the fourth image, and the second image. Since the illumination light forming these images is in the infrared wave region, it is out of the range of sensation of the human eye, thus causing no trouble in observation of finder image. For this purpose, the wavelength of the illumination light is preferably longer than 700 nm, and more preferably longer than 750 nm, which is never sensed by any human eyes, regardless of differences between individuals.

The light reflected by the observer's eye travels backward in the path via the mirror 10 and the lens 11 then to be reflected by the half mirror 12 and thereafter to be received by the photoelectric converter 14. It is preferred that a filter for cutting the visible light but transmitting the infrared light be set in the optical path after the reflected light is separated from the finder optical path and before it is received by the photoelectric converter. The filter is for cutting the reflection light from the cornea, of the visible light of the finder image, and for photoelectrically converting only reflection light of the infrared illumination light, which is significant as light signals, into electric signals. A photoelectric surface is located at such a position that the overall power of the lens 11 and the rear surface of eyepiece lens 9 forms an image of the vicinity of the front surface of the lens, i.e., an image of the vicinity of the pupil of the observer's eye. By this arrangement, the reflection light is received while the first, second, and fourth Purkinje images are focused, but the third Purkinje image, an amount of reflection light of which is not necessarily weak, is defocused so as to diffuse the light, which presents little contribution to photoelectric signals.

Next described is the principle of operation of the part of visual axis detecting apparatus in this example. In the apparatus of FIG. 13, the infrared illumination light source 13 is a point light source and the position of illumination point light source 13 is adjusted so as to emit light at the position of the screen center on the focus plate 7. In this case, when the optical axis of the observer's eyeball passes the screen center, the illumination light source is located on an extension line of the optical path of eyeball. Thus, the Purkinje images are aligned as point images on the optical axis of eyeball. FIG. 16A shows the appearance of the vicinity of the pupil of the eyeball as observed from the front thereof. In the drawing, numeral 41 designates the iris, 42 the pupil, and 43 the superimposed Purkinje images. The brightly illuminated iris is observed in a ring shape and a bright spot of the superimposed Purkinje images from the respective surfaces is observed at the center of the dark, circular pupil 42. On the other hand, when the eyeball rotates left or right to direct the visual axis in an offset direction, the illumination light is obliquely incident thereinto with respect to the optical axis of eyeball. Thus, the Purkinje images move from the pupil center to offset positions. Further, because directions and amounts of movement are different depending upon the reflection surfaces, a plurality of Purkinje images 43, 44, . . . are observed from the front. FIG. 16B shows this state. When the optical axis of the observer's eye is directed to a position further away from the screen center, the above tendency is further enhanced, as shown in FIG. 16C Also, when the observer's eye is directed in the opposite direction, the directions of movement of the Purkinje images are also reversed.

The direction of the visual axis can be detected by converting this motion into an electric signal and performing signal processing.

FIG. 17A shows an example of positional relation between the first Purkinje image 62, the fourth Purkinje image 63, the pupil 61, and a photoelectric converting element array 64 when only horizontal movement of the visual axis is detected, and FIG. 17B diagrammatically shows outputs from respective photoelectric converting elements. Higher outputs on both sides represent the iris, and signals 65, 66 are obtained corresponding to the first Purkinje image and the fourth Purkinje image, respectively, in the dark pupil portion. The pupil center is obtained as a middle point between edge portions 67 and 68. Then the direction of the visual axis can be calculated by obtaining a distance between the pupil center and the first or fourth Purkinje image.

If knowledge of vertical and horizontal changes are desired, a two-dimensional array of photoelectric elements, for example, as shown in FIG. 18, may be prepared, whereby coordinates of the first Purkinje image 62 can be determined from a number of column 71 and a number of row 72 in the photoelectric conversion unit.

The use of a photoelectric conversion unit with a two-dimensional array of photoelectric elements can expect development of applications in broad regions including not only cameras but also image devices.

The above conventional example, however, needed to use a two-dimensional area sensor as the photoelectric conversion unit for receiving a two-dimensional reflection image of the eyeball, thus increasing the production cost of the visual axis detecting apparatus. Further, the area sensor generally has the following problems:

(1) It has fixed pattern noise (FPN) which presents fluctuations of output in each bit in a dark state. Thus, there is a possibility of error detection due to FPN in reading weak reflection signals.

(2) Since the size of each pixel must be decreased, a quantity of light is not always sufficient, which substantially lowers the sensitivity of light-receiving elements. Thus, there would be cases in which weak signals are hardly detected accurately.

SUMMARY OF THE INVENTION

It is an object of the present invention to provide a method and a means for detecting the visual axis, which enables the use a of an inexpensive 1-bit photosensor, a multi-bit line sensor, or a combination thereof without a need to use an expensive area sensor with a lot of pixels as a photoelectric conversion unit used in visual axis detecting means, and an image device having such a visual axis detecting means.

It is another object of the present invention to provide a visual axis detecting method, a visual axis detecting means, and an image device having such a visual axis detecting means, which can improve the resolution for detection of visual axis.

It is a further object of the present invention to provide a visual axis detecting method, a visual axis detecting means, and an image device having the visual axis detecting means, which can be achieved at low cost without the need to use an expensive and high-resolution photoelectric conversion unit even if it is improved in resolution for detection of the visual axis so as to become a higher-resolution system.

It is an additional object of the present invention to provide a visual axis detecting method, a visual axis detecting means, and an image device having the visual axis detecting means, which can take high output signals out of a photoelectric conversion unit and which is immune to noise.

It is still another object of the present invention to provide a visual axis detecting method, a visual axis detecting means, and an image device having the visual axis detecting means, which can detect the visual axis without a need to use a complex optical system and which can avoid error detection under circumstances with a lot of external light or stray light.

It is still another object of the present invention to provide a visual axis detecting method, a visual axis detecting means, and an image device having the visual axis detecting means, which can permit further cost reduction, further weight reduction, and further improvement in reliability.

DESCRIPTION OF THE INVENTION AND PREFERRED EMBODIMENTS

Figure 1:
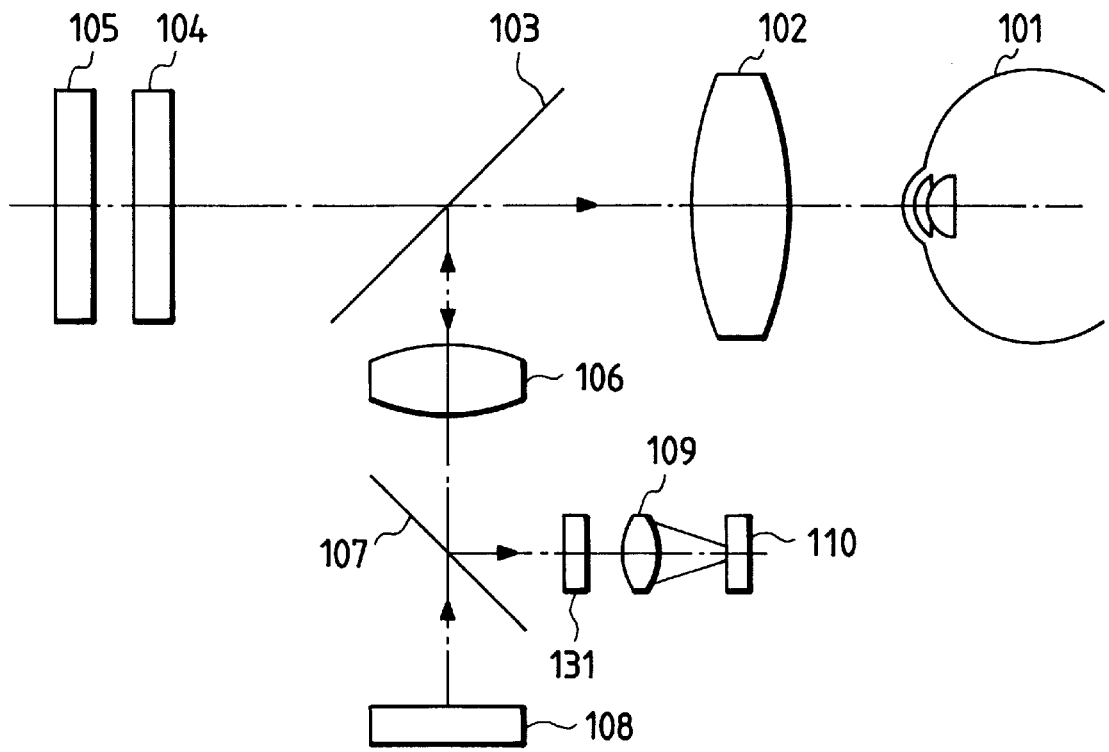
FIG. 1 is a schematic structural view for illustrating a first embodiment.

A visual axis detecting means of the present invention comprises illuminating means for illuminating an eye of an observer, photoelectric conversion means for receiving reflection light from the eye of the observer, and calculating means for calculating a direction of a visual axis of the observer, based on an output from the photoelectric conversion means, wherein the illuminating means has means for scanning the eye with illumination light.

An image device of the present invention has a display unit for an observer to observe; a visual axis detecting means comprising illuminating means for illuminating an eye of the observer, photoelectric conversion means for receiving reflection light from the eye of the observer, and calculating means for calculating a direction of a visual axis of the observer, based on an output from the photoelectric conversion means; and control means for controlling a signal output into the image device or out of the image device, based on information for the visual axis from the visual axis detecting means.

A visual axis detecting method of the present invention comprises the steps of scanning an eye of an observer with illumination light from illuminating means to illuminate it, receiving reflection light from the eye of the observer based on the illumination light by means of photoelectric conversion means in synchronization with the scanning, and detecting a visual axis of the observer using an output from the photoelectric conversion means and a timing of the scanning.

The previously described objects are achieved by these embodiments of the present invention.

The present invention provides a visual axis detecting method, a visual axis detecting means, and an image device having the visual axis detecting means, which can use an inexpensive 1-bit photoelectric conversion element, an inexpensive multi-bit line sensor, or a combination thereof without a need to use an expensive area sensor with a lot of pixels as a photoelectric conversion unit used in visual axis detecting means.

Also, the present invention provides a visual axis detecting method, a visual axis detecting means, and an image device having the visual axis detecting means, which can improve the resolution for detecting the visual axis.

Further, the present invention provides a visual axis detecting method, a visual axis detecting means, and an image device having the visual axis detecting means, which can be achieved at low cost without a need to use an expensive and high-resolution photoelectric conversion unit even if it is improved in resolution for detection of visual axis so as to become a higher-resolution system.

In addition, the present invention provides a visual axis detecting method, a visual axis detecting means, and an image device having the visual axis detecting means, which can take high output signals out of a photoelectric conversion unit and which is immune to noise.

Also, the present invention provides a visual axis detecting method, a visual axis detecting means, and an image device having the visual axis detecting means, which can detect the visual axis without a need to use a complex optical system and which can avoid error detection even under circumstances with a lot of external light or stray light.

Further, the present invention achieves further cost reduction, further weight reduction, and further improvement in reliability.

The present invention will be described in detail with specific embodiments thereof. It is intended that the present invention not be limited to these embodiments but that the present invention involve embodiments and modifications including replacement of elements or design changes within the scope wherein the objects of the present invention can be achieved.

Embodiment 1

Figure 2:
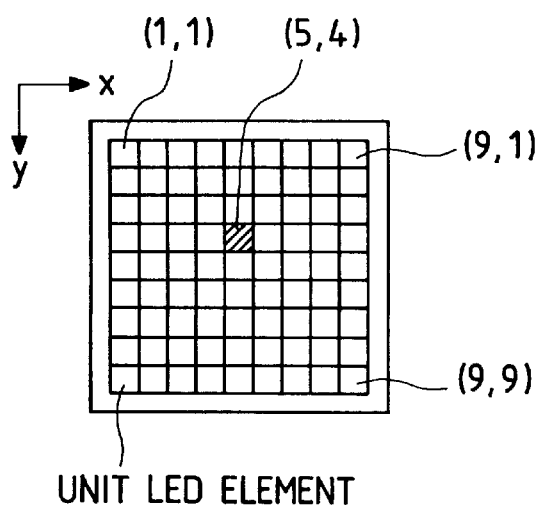
FIG. 2 is a schematic plan view for illustrating a light source in the first embodiment.

The first embodiment of the present invention is now described referring to FIG. 1 and FIG. 2, in which the present invention is applied to a viewfinder of a video camera as an image device.

FIG. 1 is a schematic structural view for illustrating the structure of the viewfinder of the present embodiment, and FIG. 2 is a schematic plan view for illustrating a light source used in the present embodiment.

In FIG. 1, reference numeral 101 designates an eyeball of an observer, 102 an eyepiece lens, 103 a half mirror, 104 a liquid crystal panel as a display unit, 105 a backlight for illuminating the liquid crystal panel 104 from the back face thereof, 106 a condenser lens, 107 a half mirror, 108 a light source (infrared light source) for emitting illumination light used in detection of visual axis, 109 a condenser lens, 110 a photoelectric conversion unit, and 131 a visible light cutting filter. When light from the backlight 105 passes through the liquid crystal panel 104 to enter the eyeball 101, the observer can observe a finder image displayed on the liquid crystal panel 104 through the eyepiece lens 102 and the half mirror 103.

For detection of the visual axis of the observer, light emitted from the light source 108 is guided through the half mirror 107 and the condenser lens 106 to reach the half mirror 103. The light is bent by the half mirror 103 to illuminate the eyeball 101 through the eyepiece lens 102.

Reflection light resulting from the illumination of eyeball 101 travels again through the eyepiece lens 102 to reach the half mirror 103. There, it is again bent by the half mirror 103 then to reach the half mirror 107. The reflection light is then bent by the half mirror 107 to enter the visible light cutting filter 131. After the visible light cutting filter 131 filters out visible light components, which are all components other than the light emitted from the light source 108, the filtered light is condensed by the condenser lens 109 to enter the photoelectric conversion unit 110.

Here, the present embodiment can employ the previously described method of detecting the visual axis as the fundamental principle of detection of visual axis. Namely, the present embodiment can also detect the visual axis, based on arithmetic processing by properly selecting information on the iris image, the pupil image, and the Purkinje images included in the reflection light.

The present embodiment uses a light source as shown in FIG. 2, as the light source 108 for illuminating the eyeball 101. To prevent the observer from experiencing glare or excessive light, the wavelength of the light emitted from the light source 108 should be preferably selected within a wavelength range not negatively affecting the eyeball 101 but enabling the supply of a sufficient amount of light. Taking this point into consideration, the light source 108 is preferably of infrared light and/or near infrared light. Specifically describing it with specific wavelengths, it is desired to use light of a wavelength preferably not less than 700 nm, more preferably not less than 750 nm, or light having a peak or a principal light amount in that region.

The light source 108 in the present embodiment is arranged as shown in FIG. 2. The light source 108 is composed of unit LED elements arranged in a two-dimensional array, for example, point light sources horizontally and vertically arranged in an array of 9×9=81 elements. A total number of unit LED elements and a number of vertical elements or horizontal elements can be changed with necessity. Normally, the more the elements, the better the resolution of detection. Each point light source is arranged to be turned on or off independently of the other point sources by scanning means, for example, by an electric circuit.

The photoelectric conversion unit 110 in the present embodiment is one having 1-bit or several-bit pixels, which are, for example, CCDs or photodiodes.

Next described is the visual axis detecting method in the present embodiment.

The point light sources in the light source 108 are successively turned on and off, for example, starting from the point of coordinates (1, 1), points (1, 2), (1, 3), . . . , (2, 1), (2, 2), . . . , (9, 9) follow. Beams from the respective point light sources pass at spatially different angles through the lenses, thus impinging on different points on the eyeball 101 to effect scanning.

Reflection light as reflected by the eyeball 101 passes in the previously described path then to enter the photoelectric conversion unit 110. Since the light source 108 is so arranged that the LED elements successively blink one by one, the reflection light from the respective LED elements is incident in time series into the photoelectric conversion unit 110. Integration of these time-series reflection beams makes it possible to observe an eyeball image of the eyeball 101 to be observed. Then the direction of the visual axis can be determined by detecting and calculating the Purkinje images, the iris image, and the pupil image from the eyeball image as necessary.

Describing a specific example, the center position of eyeball 101 can be determined by obtaining a horizontal middle point from the iris image or the pupil image, and further, the direction of deviation of the visual axis from the eyeball center, i.e., the direction of the visual axis can be obtained additionally using the information on detection positions of the Purkinje images.

Of course, the order of the scanning direction of the LED elements is not limited to the above order. Namely, the main scan can be performed in the horizontal direction in the order of (1, 1), (2, 1), (3, 1), . . . , (9, 1), (2, 1), . . . , (9, 9), or only a desired region can be scanned without using all of the LED elements for the entire region of the LED elements.

Here, because it is normally easier as to the movement of the visual axis to capture the visual point of display image in the horizontal direction rather than in the vertical direction, and because there are upper and lower cilia and palpebrae for an actual eyeball 101, whose information increases the noise, scanning of the LED elements should be preferably arranged in the transverse direction with respect to the eyeball, considering detection of the center position of the eyeball within a shorter time.

Based on the above constitution and method, the present embodiment can provide a visual axis detecting method and visual axis detecting means, low in cost, easy in size reduction, and free of influence of external light or the like.

Figure 3A:
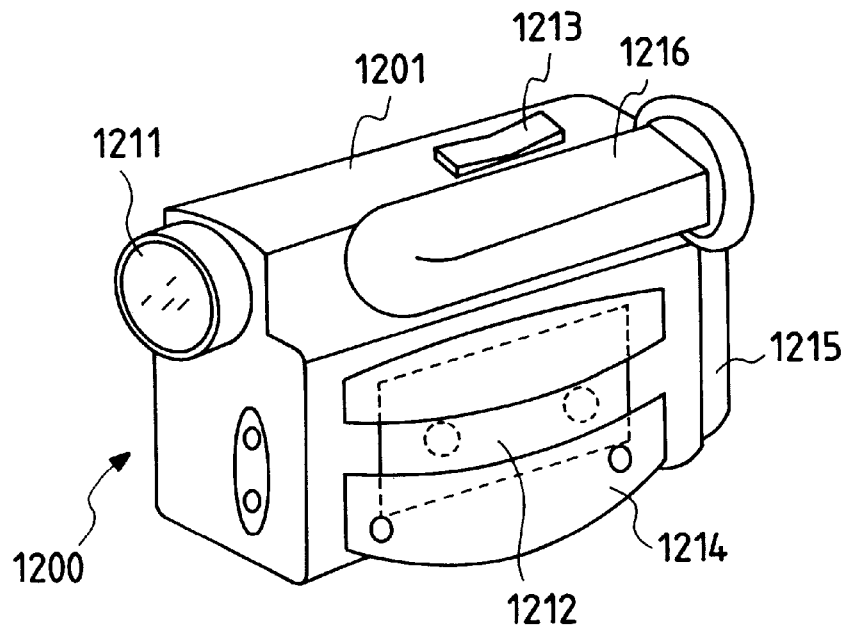
FIG. 3A is a schematic view of an image device to which the embodiment of the invention can be applied, and FIG. 3B a schematic block diagram thereof.
Figure 3B:
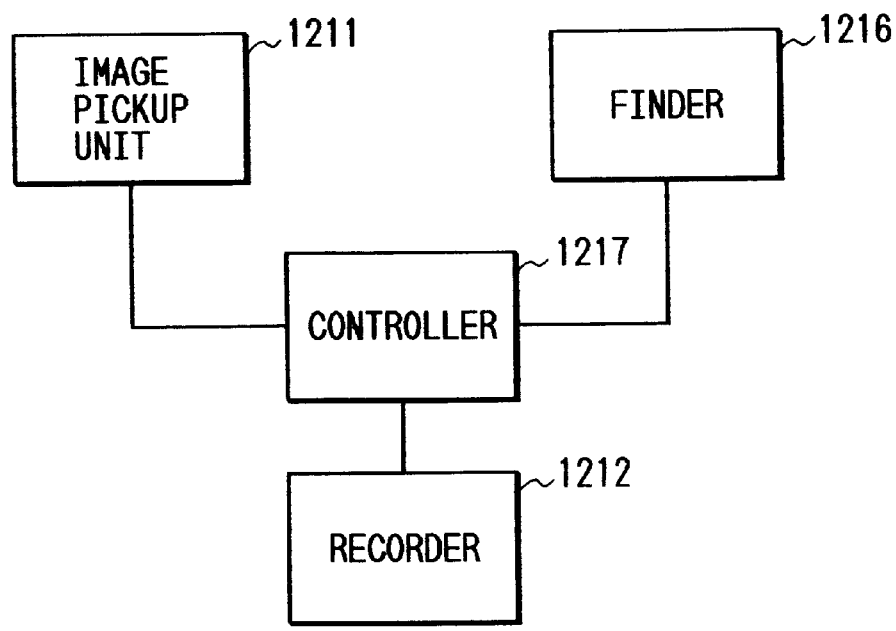

FIGS. 3A and 3B show an overall schematic view and a schematic block diagram of a video camera 1200 including a built-in electronic viewfinder according to the present embodiment. In FIGS. 3A and 3B, a main body 1201 has an image pickup unit 1211, a recording unit 1212, and a finder unit 1216. Observing a video picture through the finder, a camera operator records incident images through the taking lens in the recording unit. Numeral 1213 is a zooming switch, which drives the taking lens so as to change the size of recording images. Numeral 1214 designates an auxiliary part for holding the hand of camera operator, which is a band made of soft skin or fabric. Also, a charging-type battery 1215 is mounted as a power source for the entire apparatus.

In the finder 1216 there are stored the visual axis detecting means and the display unit as described with FIG. 1 in the present embodiment.

Further, the camera has a control unit 1217 having a CPU and a memory for controlling the image pickup unit 1211, finder unit 1216, and recording unit 1212 with necessity. Power is supplied from the light source to the image pickup unit 1211, finder unit 1216, recording unit 1212, and control unit 1217.

The video camera constructed in the above manner has the visual axis detecting means as described in the present embodiment whereby, based on the information on the detected visual axis, the control unit 1217 can detect which way the visual axis is directed and the focus position and exposure of the image pickup unit 1211 can be changed if necessary. Also, using the information on visual axis as a switch, the camera can control the recording start of the recording unit 1212, a change in quantity of light of the backlight for the display unit in the finder portion 1216, a change in contrast, etc., as necessary.

Figure 4A:
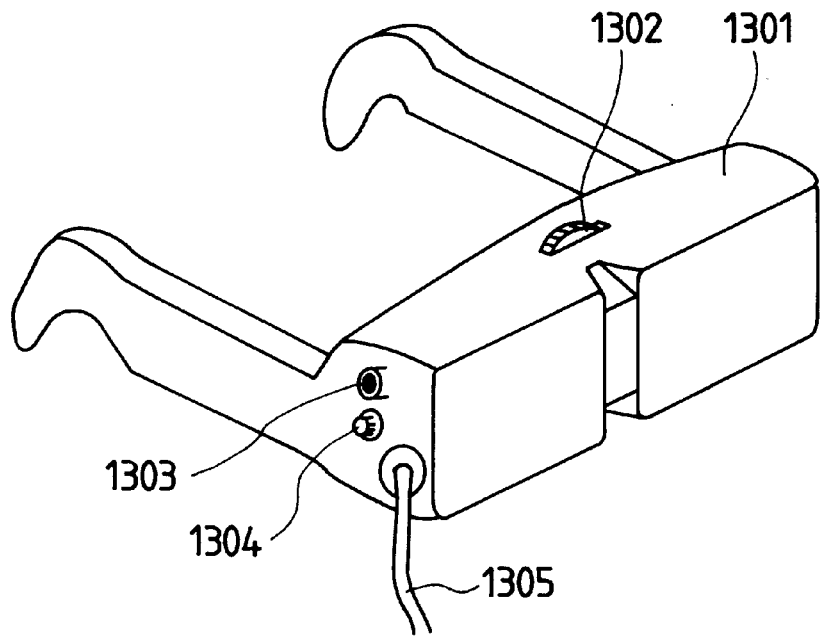
FIG. 4A is a schematic view of an image device to which the embodiment of the invention can be applied.
Figure 4B:
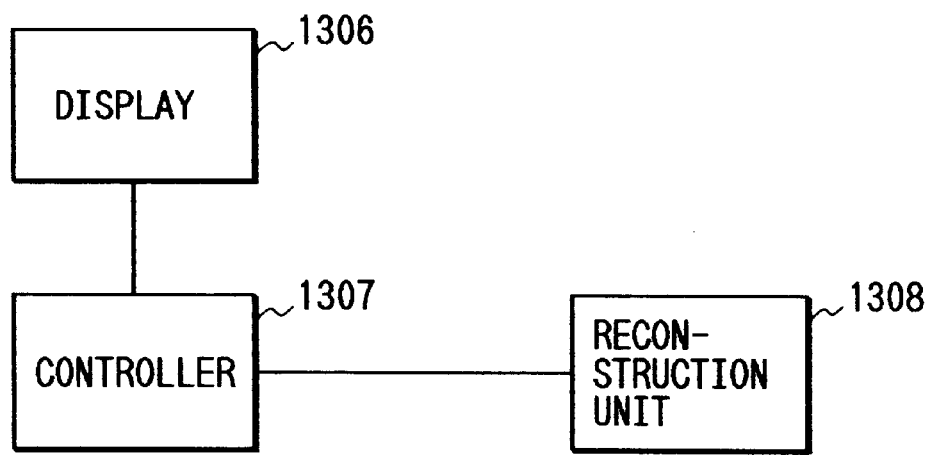
FIG. 4B is a schematic block diagram thereof.

Further described with FIGS. 4A and 4B is an example in which the visual axis detecting means of the present embodiment is applied an HMD (Head Mounted Display), also known as a goggle-like television.

In the example an HMD shown in FIGS. 4A and 4B, the liquid crystal display panel 104 of FIG. 1 functions as a display unit for displaying image information like a popular television.

FIG. 4A is a schematic view an HMD and FIG. 4B a schematic block diagram thereof.

A main body 1301 has an eyeglass (goggle) shape, which has two liquid crystal display panels located corresponding to both eyes. Portions against the ears are formed in a hook shape, and a diopter adjusting dial 1302 is provided on the upper portion of the main body. Numeral 1303 is a power switch, which turns on or off the power supplied through a power cord 1305. Numeral 1304 is a luminance adjusting knob. Video information is supplied through a cord, similarly as the power, from a reconstructing means (not shown). The visual axis detecting means according to the present embodiment is stored inside the main body 1301. Individual visual axis detecting means may be provided for each of both eyes, but the purpose can be fully achieved even with provision of a single visual axis detecting mechanism for either one of the left and right eyes.

Further, as shown in FIG. 4B, the HMD has a display unit 1306 including the visual axis detecting means and the liquid crystal display panel, and a control unit 1307 for performing an arithmetic operation of the information on visual axis and for controlling a reconstructing unit 1308, as necessity.

The above arrangement enables switching of various switches based on the information on the visual axis, and movement of display information in accordance with movement of visual axis.

The reconstructing unit may be not only a video reproducer, but also an image device for reproducing image information from an electronic device such as a computer.

The present embodiment also can be applied to image devices other than the above devices, including still cameras.

Embodiment 2

Next described is another preferred embodiment of the present invention.

Figure 5:
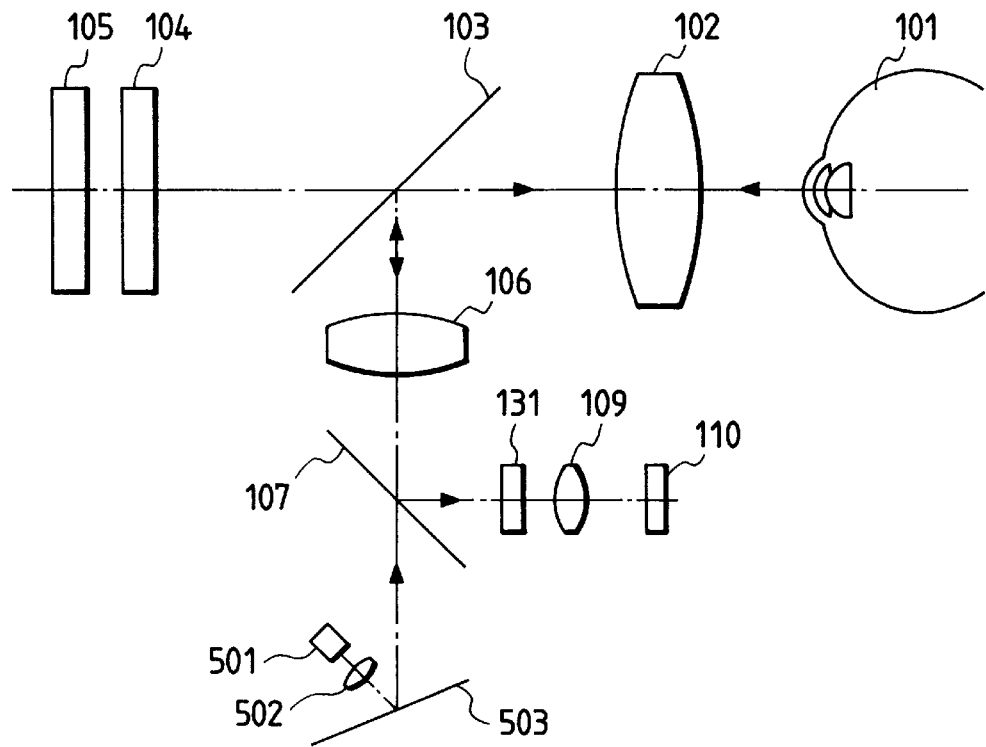
FIG. 5 is a schematic structural view for illustrating a second embodiment.

FIG. 5 is a schematic structural view for illustrating the present embodiment. Members with the same reference numerals as those in FIG. 1 represent the same members as in FIG. 1, and therefore detailed description thereof will be omitted.

Numeral 501 designates a light source, 502 a condenser lens, and 503 a movable mirror.

In the present embodiment, light from the light source 501 composed of a single element or a line of elements is mechanically deflected to scan by moving the movable mirror 503, thereby scanning the eyeball with infrared light.

After the infrared light is condensed by the condenser lens 502, it is reflected by the movable mirror 503 as scanning means to pass through the half mirror 107 and the condenser lens 106 and then to be reflected by the half mirror 103. After that, the light enters the eyeball 101. Then reflected light travels backward in the path, is reflected by the half mirror 107, and is condensed on the photoelectric conversion unit 110 by the condenser lens 109.

Signals output from the photoelectric conversion unit 110 are the same as those in the first embodiment, and therefore the same signal processing method can be employed for the detection of the visual axis herein.

The scanning of movable mirror 503 can be realized by a combination of a solenoid, a motor, a piezoelectric device, and an elastic member used therewith if necessary.

The present embodiment does not need to use a light source composed of a two-dimensional array (or area array) of elements, but can be achieved even with a single LED element, which enables further cost reduction.

In addition, a light quantity of the scanning light can be made fully large, thereby enabling a further improvement in accuracy of detection of visual axis.

Of course, the visual axis detecting means as described in the present embodiment also can be applied to the various image devices described in embodiment 1.

Embodiment 3

Figure 6:
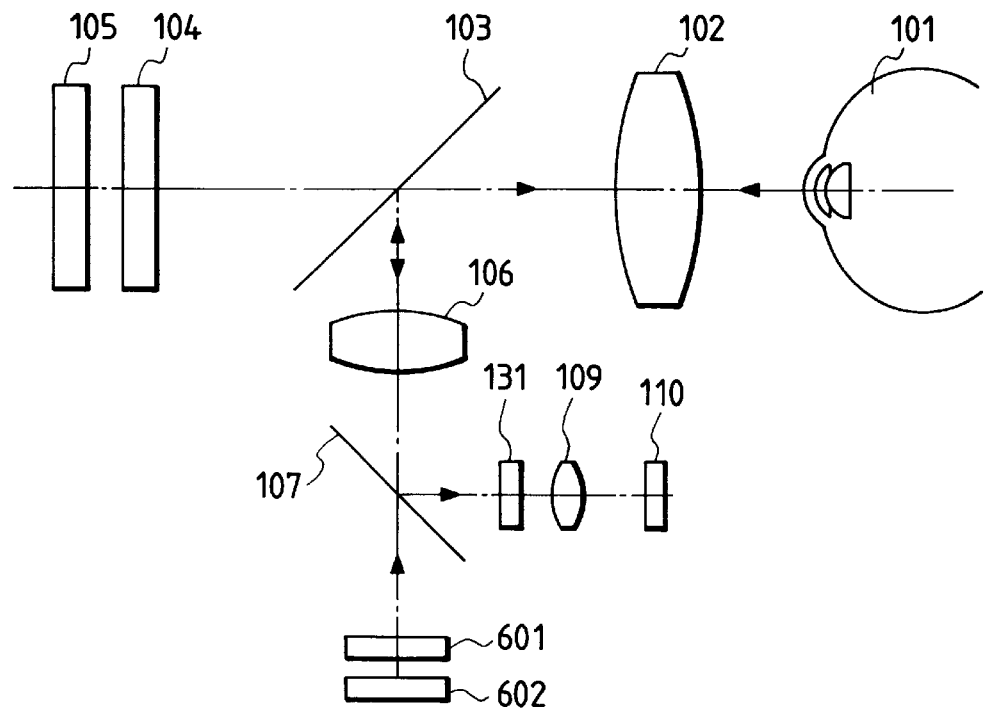
FIG. 6 is a schematic structural view for illustrating a third embodiment.

Another embodiment of the present invention is next described referring to FIG. 6.

FIG. 6 is a schematic structural view for illustrating a visual axis detecting means of the present embodiment. In FIG. 6, numeral 601 designates a liquid crystal shutter array for scanning and 602 a light source.

In the present embodiment, the liquid crystal shutter array 601 is used for scanning with a single infrared light source 602. Namely, instead of scanning infrared light, scanning signals are applied to the liquid crystal shutter array to let infrared light only at desired positions pass therethrough, thereby scanning the eyeball.

Similarly, as in embodiment 1, the scanning light passes through the half mirror 107 and the condenser lens 106 to be reflected by the half mirror 103 and thereafter to enter the eyeball 101. Reflection light travels backward in the path to be reflected by the half mirror 107 and thereafter to be condensed on the photoelectric conversion unit 110. Signals output after photoelectric conversion are the same as those in embodiment 1 or embodiment 2, and therefore the same signal processing method can be employed for detection of the visual axis herein.

The present embodiment includes no mechanically moving mechanism for scanning of the light source, so that reliability can be further enhanced. Of course, the present embodiment can achieve further cost reduction, further weight reduction, and higher accuracy.

Also, the present embodiment can be suitably applied to the various image devices as described above.

Embodiment 4

Another embodiment of the present invention is described referring to FIG. 7 to FIG. 11.

Figure 7:
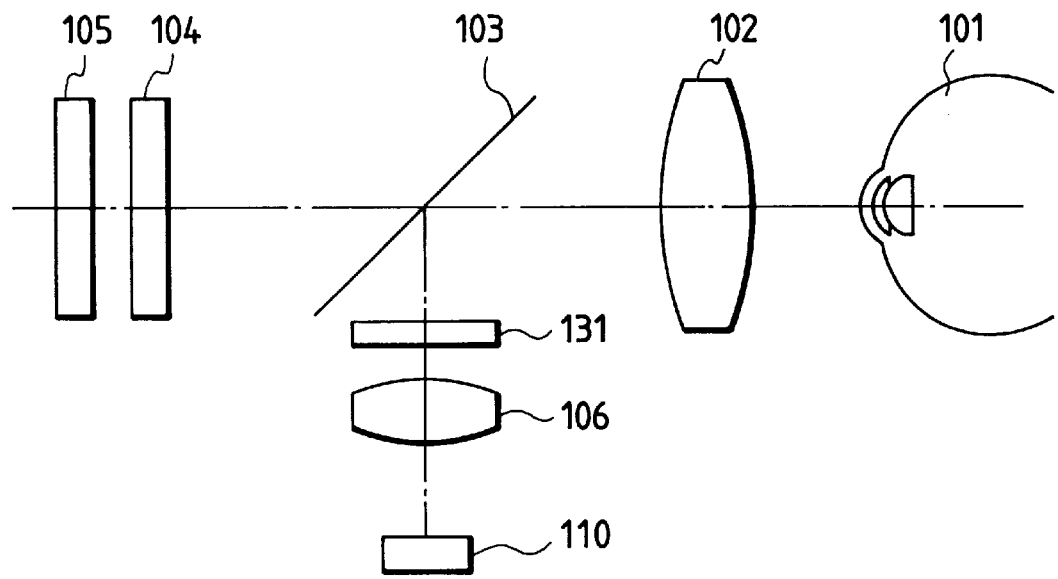
FIG. 7 is a schematic structural view for illustrating a fourth embodiment.

FIG. 7 shows schematic structure of an optical system in the present embodiment. Infrared light for detecting the visual axis is included as a component in a spectrum of backlight, which illuminates the observer's eyeball through a liquid crystal panel for display. Then, the infrared light passes through the half mirror 103 and the eyepiece lens 102 to be reflected by the eyeball 101. Reflected light travels backward in the path to be reflected by the half mirror 103 and then to be condensed by the condenser lens 106. After that, the light impinges on the photoelectric conversion unit 110.

Figure 8:
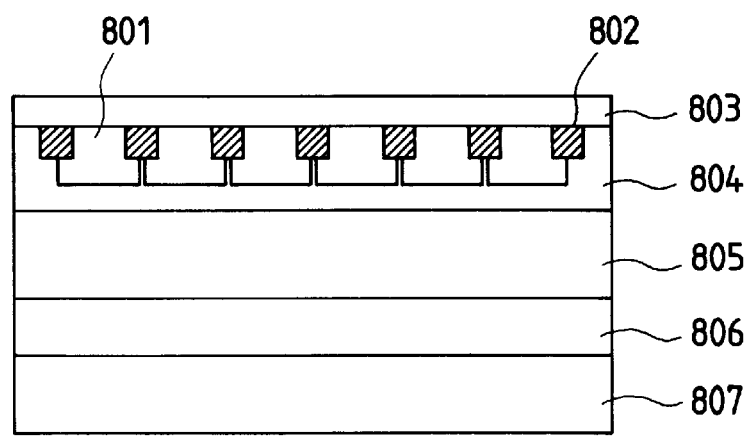
FIG. 8 is a schematic cross-sectional view for illustrating a liquid crystal panel in the fourth embodiment.
Figure 9A:
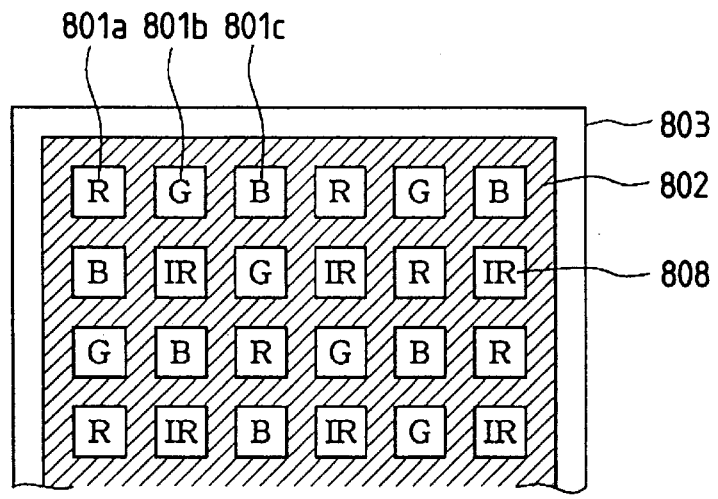
FIGS. 9A and 9B are schematic plane views for illustrating a layout of a color filter in a liquid crystal panel in the fourth embodiment.
Figure 9B:
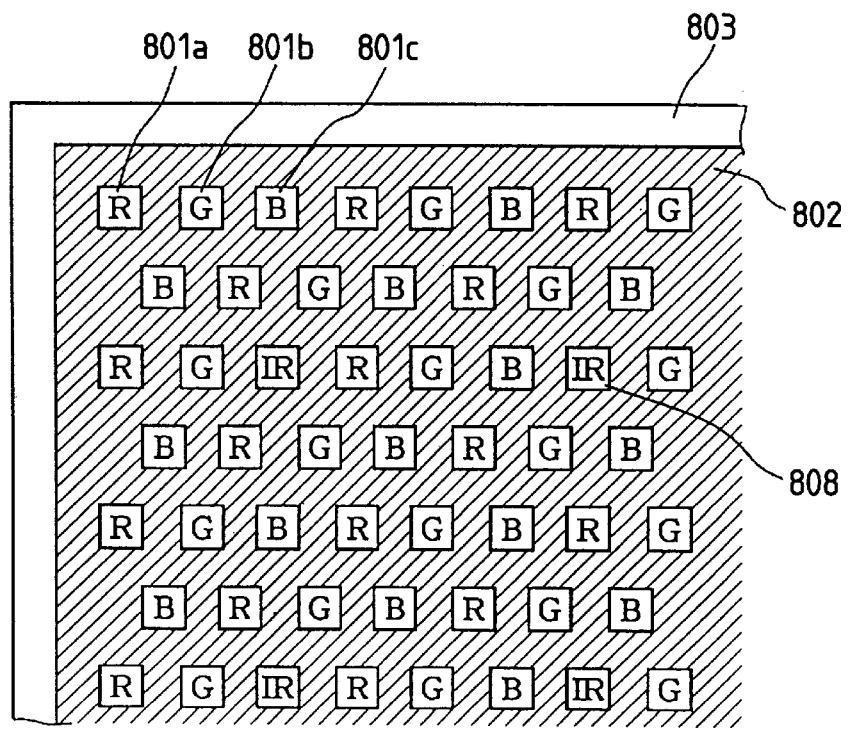

FIG. 8 is a schematic cross-sectional view of the liquid crystal panel in the present embodiment. There are laminated a liquid crystal 805, an upper electrode 804, and a color filter 801 between a glass or semiconductor substrate 807 on which a switching element 806 is formed, and a glass substrate 803 opposed to the substrate 807. The color filter is sectioned in pixels by a black matrix 802. The layout of the color filter is next described using the schematic plan views of FIGS. 9A and 9B. There are two conceivable cases: one as shown in FIG. 9A wherein pixels (801*a*, 801*b*, 801*c*) are arranged in a matrix of rows and columns; the other as shown in FIG. 9B wherein the pixels are arranged in a delta array. In FIG. 9A, for example, IR pixels (pixels for transmitting infrared light) each for displaying an infrared component are added as fourth pixels in addition to the R, G, and B pixels, as arranged in a square array of the four pixel kinds. In FIG. 9B, R, G, and B pixels are arranged in a delta array and IR pixels are arranged approximately in a ratio of one pixel per 16 pixels. How to arrange the IR pixels is just a designing matter. It is thus of course possible that another arrangement different from those in the present embodiment is employed.

Figure 10:
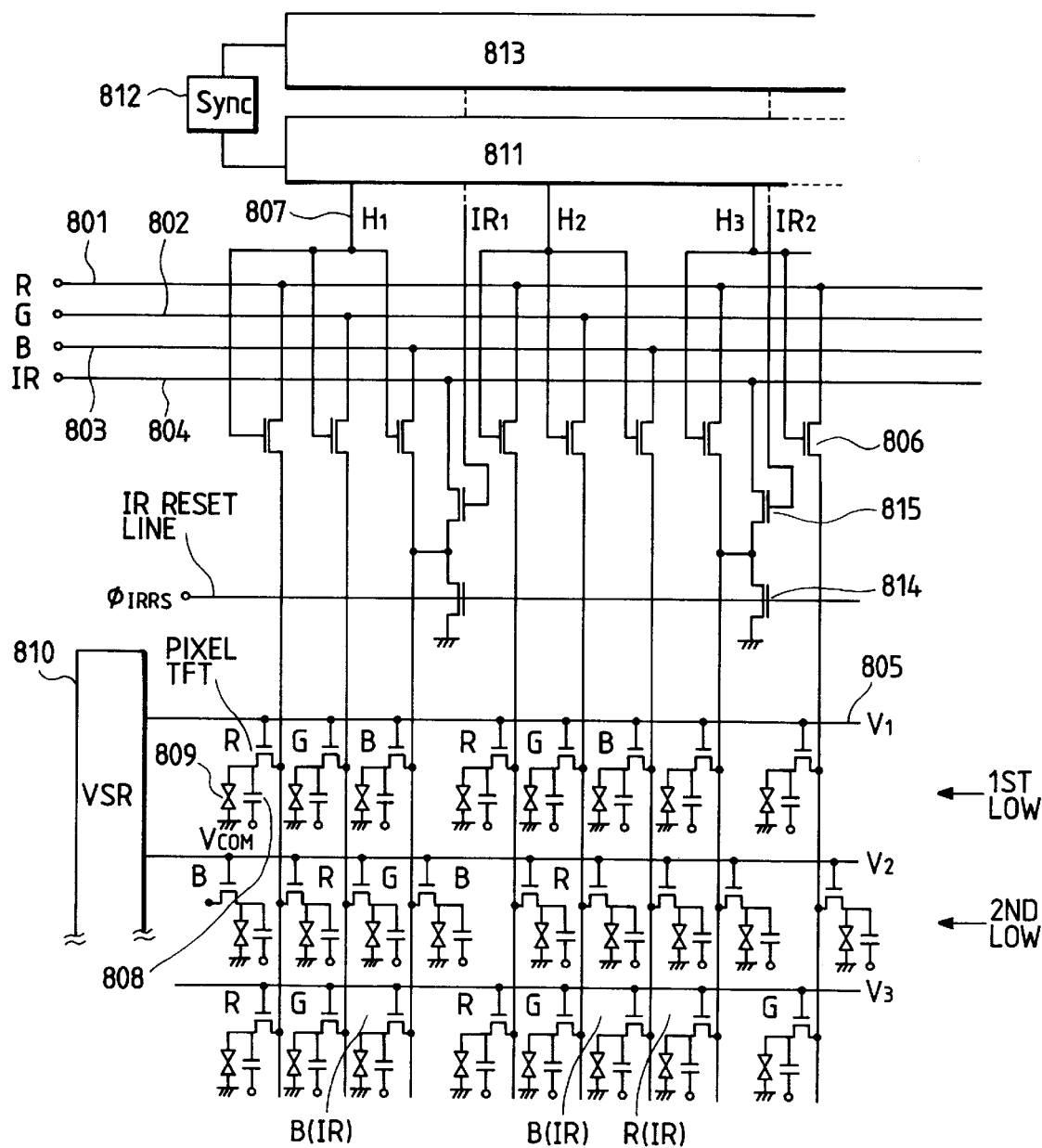
FIG. 10 is a circuit diagram for illustrating an example of a drive circuit in the liquid crystal panel in the fourth embodiment.

FIG. 10 is a diagram to show a driving circuit of the liquid crystal panel for the color filter of FIG. 9A.

Gates of pixel TFTs are connected to scanning lines 805 of vertical shift register 810 while sources thereof are connected to respective signal lines 801 to 804 of R, G, B, and IR through an associated MOS switch as a transfer gate 806. Switching of each MOS switch is effected through an output line 807 of horizontal shift register 811. Connected to a drain of each TFT is a pixel electrode for driving a holding capacitor 808 for holding the charge and a liquid crystal 809.

The image display is performed as follows. First, the TFTs in the first row selected by the vertical shift register are turned on. Signals on the respective color signal lines are written in the pixels through the transfer gates successively selected by the horizontal shift register. Then the TFTs in the first row are turned off. The same operation is repeated in the order of the second row, the third row, . . . , thus successively writing signals in pixels.

Next described is a scanning method of infrared light for detecting the visual axis. The signal line for the IR pixels is provided separately of those for image display and is connected through IR transfer gates 814 to an IR pixel shift register 813 synchronized with the horizontal shift register 811 by a synchronous circuit 812.

Figure 11:
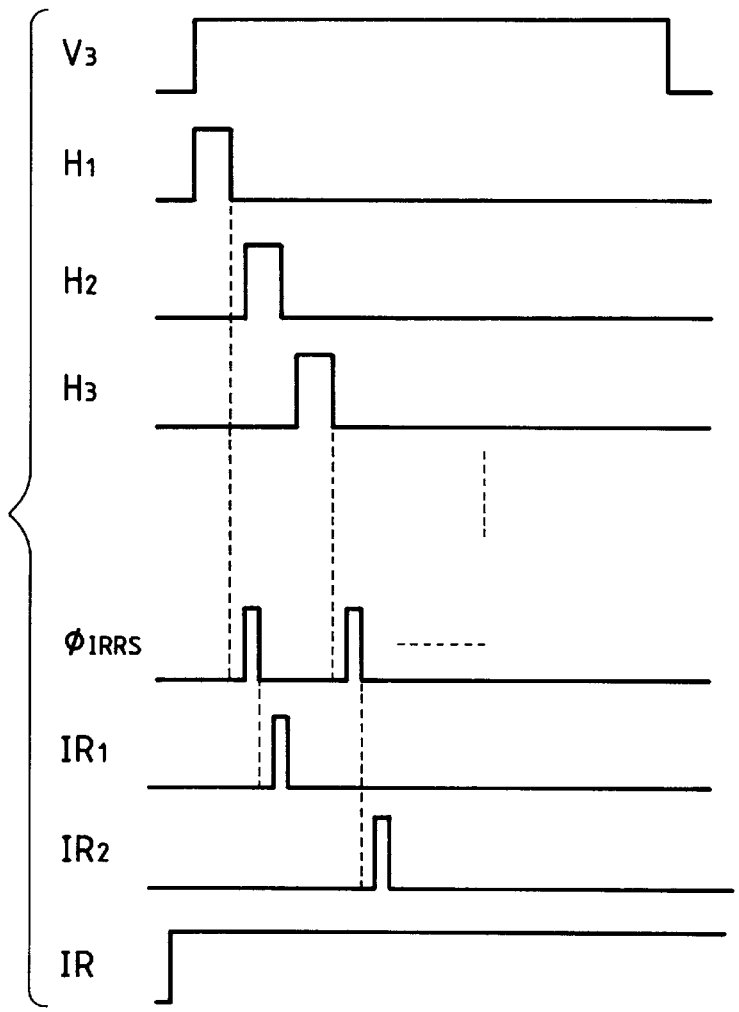
FIG. 11 is a timing chart for illustrating the drive of the liquid crystal panel in the fourth embodiment.

FIG. 11 is a timing chart of signals for writing the third row of TFTs including IR pixels. Immediately after an image signal is once written in an IR pixel, an IR reset gate 814 is turned on to discharge the charge in the pixel (of $\Phi_{IRRS}$ high level). Then a white signal (or a signal to make liquid crystal transmissive) on the IR signal line 804 is written through the IR transfer gate 814 by the IR pixel shift register. Immediately before a next IR pixel is turned on, the IR reset gate is again turned on so as to reset the previous IR pixel, thus effecting successive scanning of IR light.

The operation for successively detecting the scanning infrared light on the photoelectric conversion unit is the same as that in the other embodiments.

The present embodiment can save the space for setting the infrared light source, whereby the apparatus can be constructed in a further compact shape, at a reduced weight, and at lower cost.

It is apparent as previously described that methods of arrangement of IR pixels other than that in the present embodiment can be employed. Also, the circuit for scanning of IR light is not limited to only that in the above embodiment. Namely, any circuit can be applied as long as it can realize scanning for successively turning on and off the pixels.

The MOS switches in the circuit may be readily achieved in various forms of PMOS, NMOS, or CMOS, etc.

Embodiment 5

Figure 12:
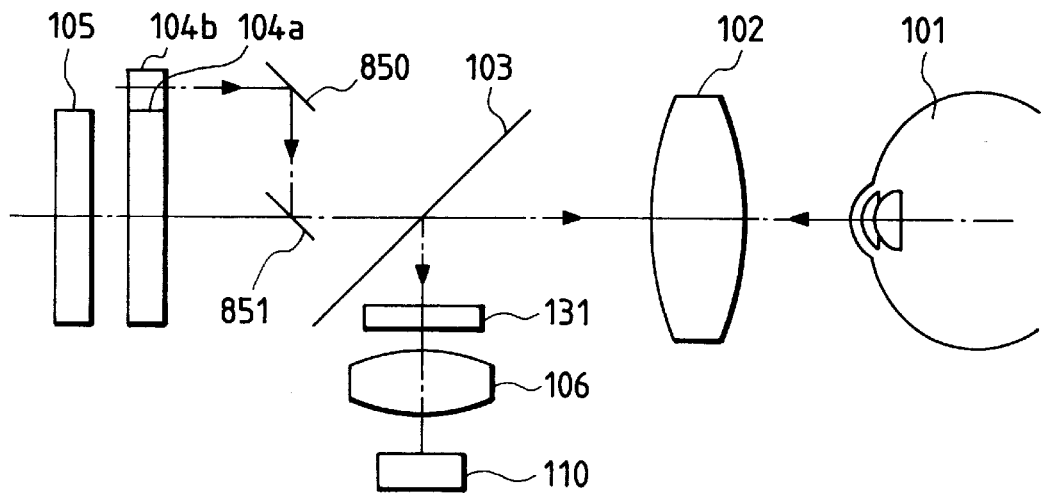
FIG. 12 is a schematic structural view for illustrating a fifth embodiment.
Figure 13:
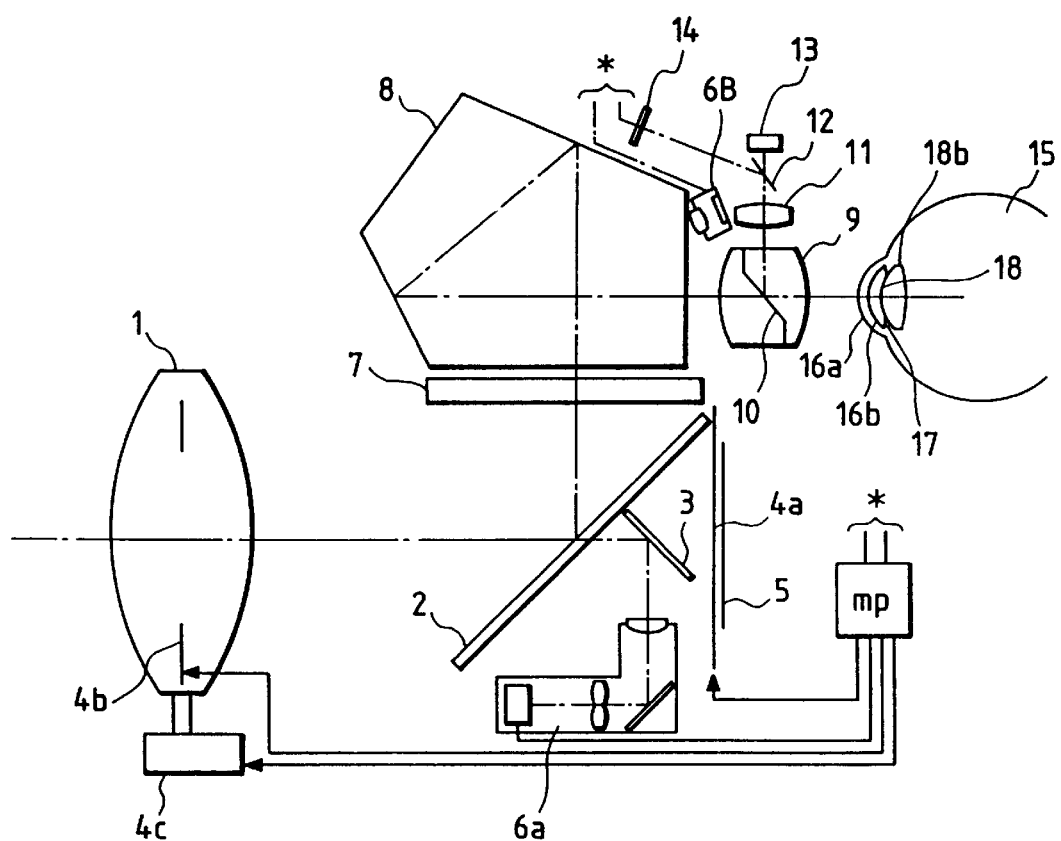
FIG. 13 is a view for illustrating a conventional visual axis detecting means.
Figure 14:
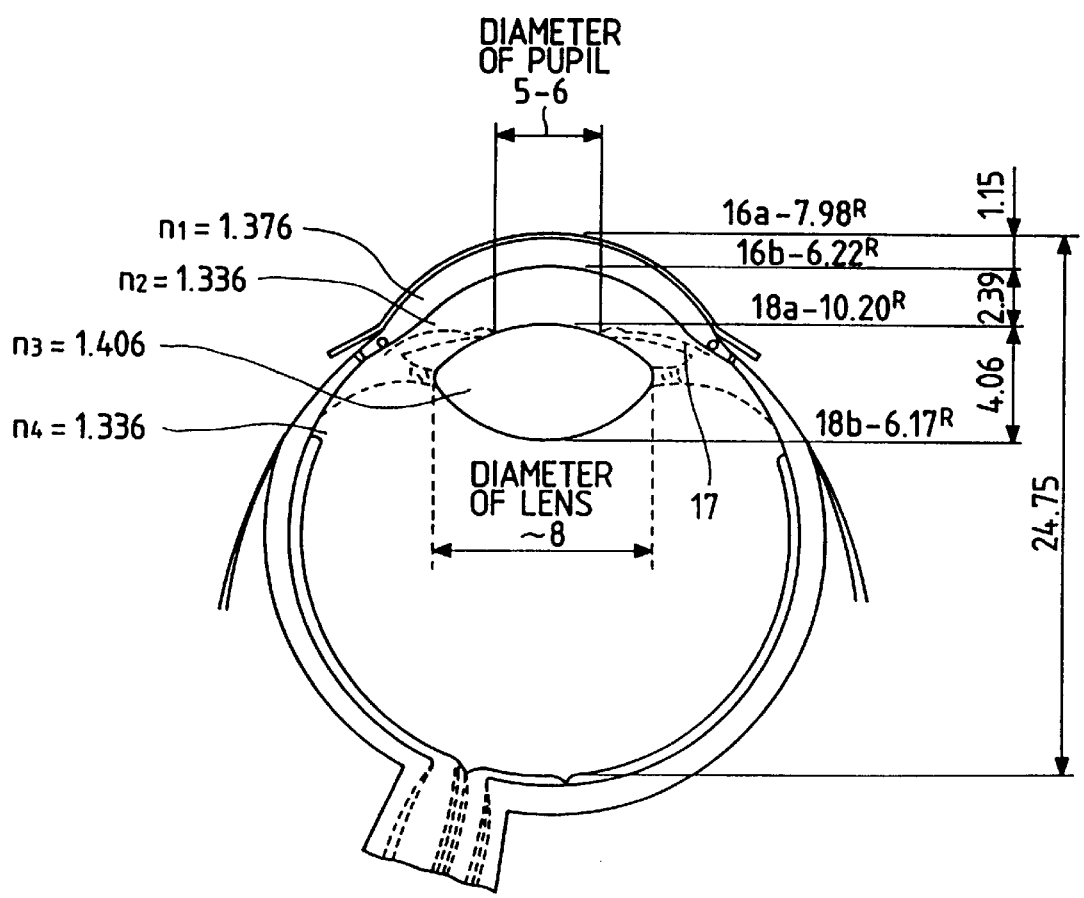
FIG. 14 is a view for illustrating refractive index changes at respective surfaces in the human eye.
Figure 15:
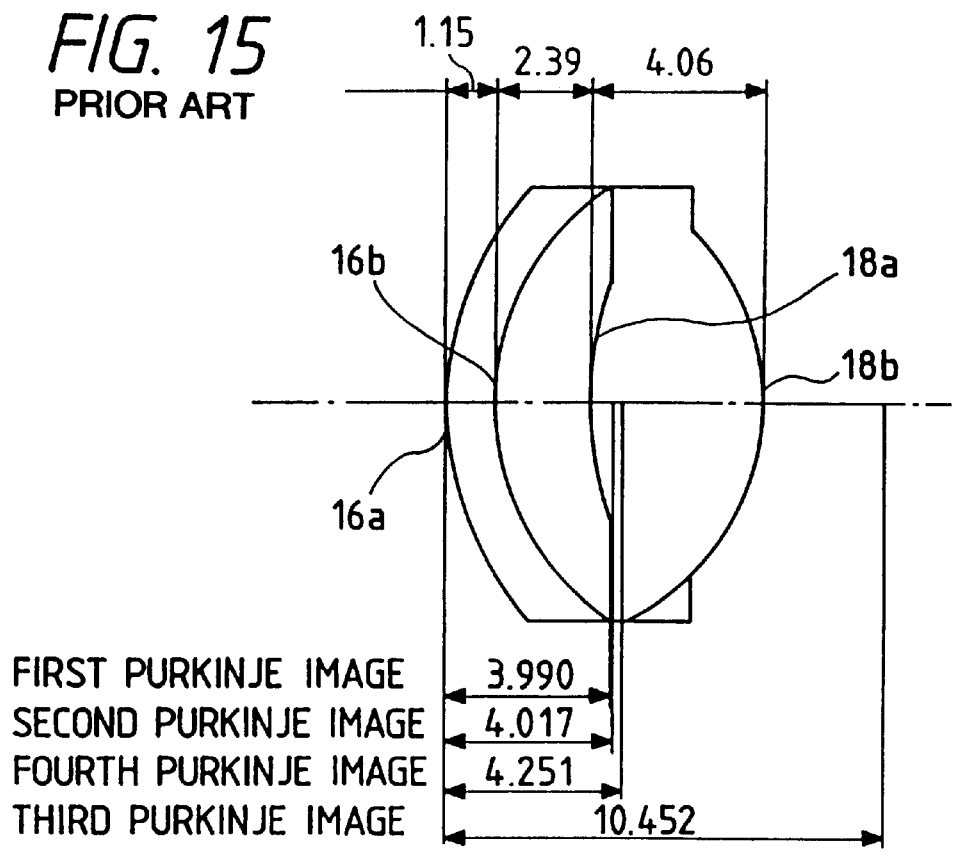
FIG. 15 is a view showing positions of Purkinje images from the respective surfaces in the human eye.

Still another embodiment of the present invention is next described referring to FIG. 12.

In the present embodiment, an infrared light source is set in the peripheral region of display area near a display panel.

The present embodiment has an infrared light source array 104*b* near the peripheral region of a liquid crystal panel 104*a*, as shown in FIG. 12, with which two-dimensional scanning is effected. The scanning light travels via a mirror 850 and a half mirror 851 to enter the eyeball. Reflection light is condensed on the photoelectric conversion unit 110, which converts the light into a signal sequence. The way for detecting the visual axis from the signals is the same as in the other embodiments.

The present embodiment can also reduce the space for the infrared light source, whereby the apparatus can be made compact in size, light in weight, and low in cost.

The infrared light source may be arranged at the four corners of a panel or at two corners thereof as necessary.

In addition, the infrared light source may be composed of LED elements and/or may utilize infrared components of backlight 105.

As detailed above, the present invention provides a visual axis detecting method, a visual axis detecting means, and an image device having the visual axis detecting means, which can use an inexpensive 1-bit photoelectric conversion element, a multi-bit line sensor, or a combination thereof without a need to use an expensive area sensor composed of a lot of pixels as the photoelectric conversion unit used in the visual axis detecting means.

Also, the present invention can provide a visual axis detecting method, a visual axis detecting means, and an image device having the visual axis detecting means, which can improve the resolution for detecting the visual axis.

Further, the present invention provides a visual axis detecting method, a visual axis detecting means, and an image device having the visual axis detecting means, which can be achieved at low cost without a need to use an expensive and high-resolution photoelectric conversion unit even if it is improved in resolution for detection of visual axis so as to become a higher-resolution system.

In addition, the present invention provides a visual axis detecting method, a visual axis detecting means, and an image device having the visual axis detecting means, which can take large output signals out of the photoelectric conversion unit.

Additionally, the present invention can provide a visual axis detecting method, a visual axis detecting means, and an image device having the visual axis detecting means, which can detect the visual axis without a need to use a complex optical system and which can avoid error detection even under circumstances with a lot of external light or stray light.

Also, the present invention can achieve further cost reduction, further weight reduction, and further improvement in reliability.

It is intended that the present invention not be limited to the above-described embodiments but that the present invention include proper modifications and replacements based on the technical idea thereof.

For example, an example of a transmission-type liquid crystal panel was described as a liquid crystal panel in the display unit, but the liquid crystal panel is by no means limited to the transmission type. Also, the display can be modified in such a manner that the liquid crystal panel is replaced by a compact CRT, an EL display, a plasma display, etc. The use of a liquid crystal panel is, however, preferable in that it can perform color display even with a compact size, light weight, and low dissipation power.

Also, the illumination of the eyeball does not always have to be made through the eyepiece lens, but may be realized by such an arrangement that necessary light is emitted from the vicinity of the eyepiece lens toward the eyeball.

What is claimed is:

1. A visual axis detecting device comprising:
   a liquid crystal display having a light source for projecting a light image onto an eye of an observer;
   illuminating means, separate from and operable independent of said light source of said liquid crystal display, for illuminating the eye of the observer with light;
   means for scanning the eye of the observer with light from said illuminating means;
   photoelectric conversion means for receiving light which has been reflected from the eye of the observer; and
   means for calculating a visual axis orientation of the eye of the observer on the basis of a scan timing of said illuminating means and the output of said photoelectric conversion means.

2. A visual axis detecting device according to claim 1, wherein said illuminating means has light-emitting elements two-dimensionally arranged.

3. A visual axis detecting device according to claim 2, wherein each light-emitting element is an LED element.

4. A visual axis detecting device according to claim 1, wherein said illuminating means has a light-emitting element or light-emitting elements arranged in an array, and said means for scanning has means for deflecting light from the light-emitting element or light-emitting elements.

5. A visual axis detecting device according to claim 4, wherein said means for deflecting is a movable mirror.

6. A visual axis detecting device according to claim 4, wherein each light-emitting element is an LED element.

7. A visual axis detecting device according to claim 1, wherein said scanning means comprises mechanical means or electrical means for scanning.

8. A visual axis detecting device according to claim 1, wherein said illuminating means comprises a display unit.

9. A visual axis detecting device according to claim 1, wherein said photoelectric conversion means is a photo transistor or CCD.

10. A visual axis detecting device according to claim 1, wherein light from said illuminating means illuminates the eye of the observer with light that has a wavelength in a predetermined wavelength region, and said visual axis detecting device further comprises a filter disposed in an optical path from the eye of the observer to said photoelectric conversion means for filtering out light components having a wavelength different from the predetermined wavelength region.

11. A visual axis detecting device according to claim 10, wherein said illuminating means illuminates the eye of the observer with light having a wavelength of 700 nm or greater, or light having a peak or principal light quantity in a range of wavelength of 700 nm or greater.

12. A visual axis detecting device according to claim 11, wherein said illuminating means illuminates the eye of the observer with light having a wavelength of 750 nm or greater, or a light having a peak or principal light quantity in a range of wavelength of 750 nm or greater.

13. An image apparatus comprising:
a liquid crystal display having a light source for projecting a light image onto the eye of an observer;
illuminating means, separate from and operable independent of said light source of said liquid crystal display, for illuminating the eye of the observer with light;
means for scanning the eye of the observer with light from said illuminating means;
photoelectric conversion means for receiving light which has been reflected from the eye of the observer;
means for calculating a visual axis orientation of the eye of the observer on the basis of a scan timing of said illuminating means and the output of said photoelectric conversion means; and
control means for controlling a signal output in the image apparatus or to an external device, on the basis of the visual axis orientation calculated by said calculating means.

14. An image apparatus according to claim 13, wherein said illuminating means has light-emitting elements two-dimensionally arranged.

15. An image apparatus according to claim 14, wherein each light-emitting element is an LED element.

16. An image apparatus according to claim 15, wherein said liquid crystal display is one selected from a liquid crystal panel, a CRT, an EL display, and a plasma display.

17. An image apparatus according to claim 16, wherein said image apparatus is one selected from a still camera, a video camera, a goggle-type display.

18. An image apparatus according to claim 15, wherein said image apparatus is one selected from a still camera, a video camera, a goggle-type display.

19. An image apparatus according to claim 14, wherein said liquid crystal display is one selected from a liquid crystal panel, a CRT, an EL display, and a plasma display.

20. An image apparatus according to claim 19, wherein said image apparatus is one selected from a still camera, a video camera, a goggle-type display.

21. An image apparatus according to claim 14, wherein said image apparatus is one selected from a still camera, a video camera, a goggle-type display.

22. An image apparatus according to claim 13, wherein said illuminating means has a light-emitting element or light-emitting elements arranged in an array, and said scanning means has means for deflecting light from said light-emitting element or light-emitting elements.

23. An image apparatus according to claim 22, wherein said means for deflecting is a movable mirror.

24. An image apparatus according to claim 23, wherein said liquid crystal display is one selected from a liquid crystal panel, a CRT, an EL display, and a plasma display.

25. An image apparatus according to claim 24, wherein said image apparatus is one selected from a still camera, a video camera, a goggle-type display.

26. An image apparatus according to claim 23, wherein said image apparatus is one selected from a still camera, a video camera, a goggle-type display.

27. An image apparatus according to claim 22, wherein said light-emitting element is an LED element.

28. An image apparatus according to claim 27, wherein said liquid crystal display is one selected from a liquid crystal panel, a CRT, an EL display, and a plasma display.

29. An image apparatus according to claim 28, wherein said image apparatus is one selected from a still camera, a video camera, a goggle-type display.

30. An image apparatus according to claim 27, wherein said image apparatus is one selected from a still camera, a video camera, a goggle-type display.

31. An image apparatus according to claim 22, wherein said liquid crystal display is one selected from a liquid crystal panel, a CRT, an EL display, and a plasma display.

32. An image apparatus according to claim 31, wherein said image apparatus is one selected from a still camera, a video camera, a goggle-type display.

33. An image apparatus according to claim 22, wherein said image apparatus is one selected from a still camera, a video camera, a goggle-type display.

34. An image apparatus according to claim 13, wherein said scanning means comprises mechanical means or electrical means for scanning.

35. An image apparatus according to claim 34, wherein said liquid crystal display is one selected from a liquid crystal panel, a CRT, an EL display, and a plasma display.

36. An image apparatus according to claim 35, wherein said image apparatus is one selected from a still camera, a video camera, a goggle-type display.

37. An image apparatus according to claim 34, wherein said image apparatus is one selected from a still camera, a video camera, a goggle-type display.

38. An image apparatus according to claim 13, wherein said illuminating means comprises a display unit.

39. An image apparatus according to claim 38, wherein said liquid crystal display is one selected from a liquid crystal panel, a CRT, an EL display, and a plasma display.

40. An image apparatus according to claim 39, wherein said image apparatus is one selected from a still camera, a video camera, a goggle-type display.

41. An image apparatus according to claim 38, wherein said image apparatus is one selected from a still camera, a video camera, a goggle-type display.

42. An image apparatus according to claim 13, wherein said photoelectric conversion means is a photo transistor or CCD.

43. An image apparatus according to claim 42, wherein said liquid crystal display is one selected from a liquid crystal panel, a CRT, an EL display, and a plasma display.

44. An image apparatus according to claim 43, wherein said image apparatus is one selected from a still camera, a video camera, a goggle-type display.

45. An image apparatus according to claim 42, wherein said image apparatus is one selected from a still camera, a video camera, a goggle-type display.

46. An image apparatus according to claim 13, wherein said liquid crystal display is one selected from a liquid crystal panel, a CRT, an EL display, and a plasma display.

47. An image apparatus according to claim 46, wherein said image apparatus is one selected from a still camera, a video camera, a goggle-type display.

48. An image apparatus according to claim 13, wherein said image apparatus is one selected from a still camera, a video camera, a goggle-type display.

49. An image apparatus according to claim 13, wherein light from said illuminating means illuminates the eye of the observer with light that has a wavelength in a predetermined wavelength region, and said image apparatus further comprises a filter disposed in an optical path from the eye of the observer to said photoelectric conversion means for filtering out light components having a wavelength different from the predetermined wavelength region.

50. An image device according to claim 49, wherein said illuminating means illuminates the eye of the observer with light having a wavelength of 700 nm or greater, or a light having a peak or principal light quantity in a range of wavelength of 700 nm or greater.

51. An image device according to claim 50, wherein said illuminating means illuminates the eye of the observer with light having a wavelength of 750 nm or greater, or light having a peak or principal light quantity in a range of wavelength of 750 nm or greater.

52. A visual axis detecting method comprising the steps of:

projecting a light image of a liquid crystal display onto an eye of an observer using a light source of the liquid crystal display;

scanning the eye of the observer with light from illuminating means separate from and operable independent of the light source of the liquid crystal display;

receiving by photoelectric conversion means light from the illumination means reflected from the eye of the observer; and detecting a visual axis of the eye of the observer based on an output of the photoelectric conversion means and a timing of said scanning step.

53. A visual axis detecting method according to claim 52, wherein said scanning step includes mechanically or electrically scanning a light source.

* * * * *

UNITED STATES PATENT AND TRADEMARK OFFICE
CERTIFICATE OF CORRECTION

PATENT NO. : 6,104,431
DATED : August 15, 2000
INVENTOR(S) : Shunsuke Inoue, et al.

It is certified that error appears in the above-identified patent and that said Letters Patent is hereby corrected as shown below:

Column 3

Figure 16A:
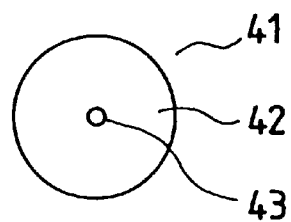
FIGS. 16A to 16C are views of the vicinity of the pupil of eyeball as observed from the front thereof.
Figure 16B:
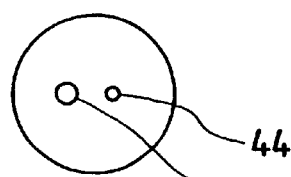
Figure 16C:
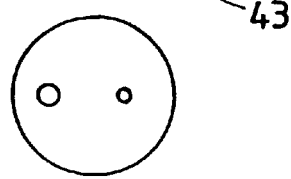
Figure 17A:
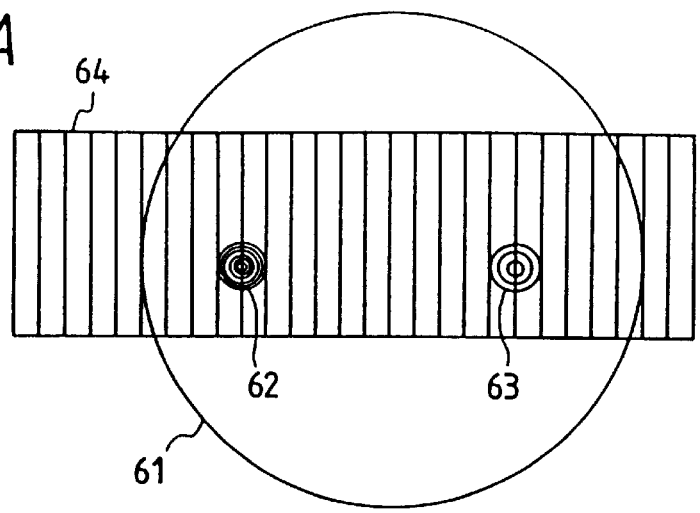
FIG. 17A is a view for illustrating detection of Purkinje images.
Figure 17B:
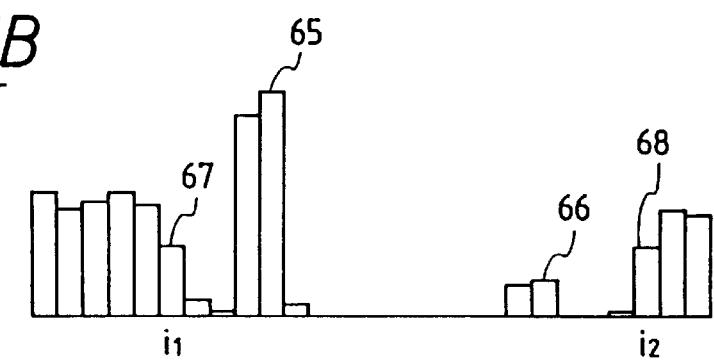
FIG. 17B is a view showing output signals.
Figure 18:
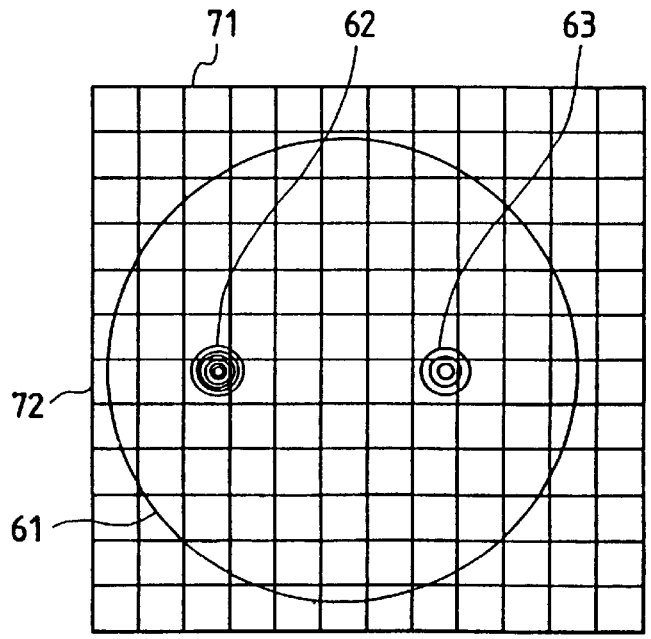
FIG. 18 is a view for illustrate two-dimensional detection of Purkinje images.

Line 11, "FIG. 16C" should read --FIG. 16C.--.
    Line 60, "a" (first occurrence) should be deleted.

Column 5

Line 6, "illustrate" should read --illustrating--.

Column 6

Line 34, "filter. When" should red --filter. ¶ When--.

Column 7

Line 42, "image" should read --image,--.

UNITED STATES PATENT AND TRADEMARK OFFICE
CERTIFICATE OF CORRECTION

PATENT NO. : 6,104,431

DATED : August 15, 2000

INVENTOR(S) : Shunsuke Inoue, et al.

It is certified that error appears in the above-identified patent and that said Letters Patent is hereby corrected as shown below:

Column 3

Line 11, "FIG. 16C" should read --FIG. 16C.--.
    Line 60, "a" (first occurrence) should be deleted.

Column 5

Line 6, "illustrate" should read --illustrating--.

Column 6

Line 34, "filter. When" should red --filter. ¶ When--.

Column 7

Line 42, "image" should read --image,--.

Signed and Sealed this

Twenty-ninth Day of May, 2001

Attest:

NICHOLAS P. GODICI

*Attesting Officer*    *Acting Director of the United States Patent and Trademark Office*